(12) United States Patent
Jhaveri et al.

(10) Patent No.: US 10,074,084 B1
(45) Date of Patent: Sep. 11, 2018

(54) SYSTEM AND METHOD FOR ADVANCED IDENTIFICATION OF A CUSTOMER TO DECREASE WAIT TIME FOR PRESCRIPTION

(75) Inventors: Nimesh S. Jhaveri, Kildeer, IL (US); Archana Dhruve, Bartlett, IL (US); Heather K. Hill, Barrington, IL (US); Dejan Kozic, Wadworth, IL (US); Laura Jean Tebbe, Antioch, IL (US); Susan G. Heald, Buffalo Grove, IL (US); Warit Tulyathorn, Chicago, IL (US); Mark A. Jones, Evanston, IL (US); Sara B. Frisk, Chicago, IL (US); Jennifer M. Levin, Chicago, IL (US); Jennifer A. Comiskey, Chicago, IL (US); David T. Blanchard, Evanston, IL (US)

(73) Assignee: WALGREEN CO., Deerfield, IL (US)

( * ) Notice: Subject to any disclaimer, the term of this patent is extended or adjusted under 35 U.S.C. 154(b) by 0 days.

(21) Appl. No.: 13/286,909

(22) Filed: Nov. 1, 2011

Related U.S. Application Data

(60) Provisional application No. 61/408,903, filed on Nov. 1, 2010.

(51) Int. Cl.
*G06Q 20/20* (2012.01)
*G06Q 10/08* (2012.01)
(Continued)

(52) U.S. Cl.
CPC ......... *G06Q 20/20* (2013.01); *G06Q 10/0836* (2013.01); *G06Q 10/109* (2013.01); *G07F 7/10* (2013.01)

(58) Field of Classification Search
CPC .............................. G06Q 50/22; G06Q 50/24
(Continued)

(56) References Cited

U.S. PATENT DOCUMENTS 6,439,345 B1 * 8/2002 Recktenwald et al. ......... 186/55
6,711,460 B1 * 3/2004 Reese ........................... 700/216
(Continued)

OTHER PUBLICATIONS

U.S. Appl. No. 14/288,087, filed May 27, 2014.
(Continued)

*Primary Examiner* — Elaine L Gort
*Assistant Examiner* — Devin C Hein
(74) *Attorney, Agent, or Firm* — Marshall, Gerstein & Borun LLP; Randall G. Rueth

(57) ABSTRACT

In a method for advanced identification of a customer of a pharmacy, identification information of the customer is received at a first pharmacy computing device after an arrival of the customer at a pharmacy location and before an arrival of the customer at a pharmacy pick-up area of the pharmacy location. An identification of the customer is generated based on the received identification information. The identification of the customer is sent to a second pharmacy computing device. Using the second pharmacy computing device, and based on the second pharmacy computing device receiving the identification, an indication is provided to a pharmacy employee that the customer has arrived at the pharmacy location to pick up a previously prepared pharmacy order and that the pharmacy employee is to obtain the previously prepared pharmacy order for pickup by the customer before the arrival of the customer at the pharmacy pick-up area.

7 Claims, 9 Drawing Sheets

(51) Int. Cl.
*G06Q 10/10* (2012.01)
*G07F 7/10* (2006.01)

(58) Field of Classification Search
USPC .......................................................... 705/2, 3
See application file for complete search history.

(56) References Cited

U.S. PATENT DOCUMENTS

| | | |
|---|---|---|
| 2002/0016740 A1* | 2/2002 | Ogasawara ..................... 705/26 |
| 2002/0128850 A1* | 9/2002 | Chen .................... G06Q 10/047 |
| | | 705/301 |
| 2002/0143592 A1* | 10/2002 | Nishikawa et al. ............... 705/7 |
| 2002/0178107 A1* | 11/2002 | Biancavilla ..................... 705/37 |
| 2004/0266335 A1* | 12/2004 | Usui et al. ................... 455/3.03 |
| 2006/0111053 A1* | 5/2006 | Wu ..................... G06K 17/0022 |
| | | 455/90.3 |
| 2006/0111941 A1* | 5/2006 | Blom ................................ 705/2 |
| 2006/0163349 A1* | 7/2006 | Neugebauer .................. 235/383 |
| 2007/0088624 A1* | 4/2007 | Vaughn .................. G06Q 30/02 |
| | | 705/15 |
| 2010/0057532 A1* | 3/2010 | Sanguinetti et al. ........... 705/10 |
| 2012/0030726 A1* | 2/2012 | Winter et al. ................. 725/114 |

OTHER PUBLICATIONS

Office Action for U.S. Appl. No. 14/288,087, dated Mar. 27, 2015.
Final Office Action for U.S. Appl. No. 14/288,087, dated Jul. 16, 2015.
Office Action for U.S. Appl. No. 14/288,087, dated Dec. 18, 2015.

* cited by examiner

Please enter your personal information below:

Last name: _____ 504

First name: _____ 506

Home Address: _____ 508

Prescription Number: _____ 510

Date of Birth: __/__/__ 512

SYSTEM AND METHOD FOR ADVANCED IDENTIFICATION OF A CUSTOMER TO DECREASE WAIT TIME FOR PRESCRIPTION

CROSS-REFERENCE TO RELATED APPLICATION

The present application claims the benefit of U.S. Provisional Patent Application No. 61/408,903, entitled "SYSTEM AND METHOD FOR ADVANCED IDENTIFICATION OF A CUSTOMER TO DECREASE WAIT TIME FOR PRESCRIPTION," filed on Nov. 1, 2010, the entire disclosure of which is hereby incorporated by reference herein.

TECHNICAL FIELD

The present disclosure relates generally to prescription transactions at a pharmacy and, more particularly, to identifying a pharmacy customer in advance of a prescription transaction.

BACKGROUND

In many cases, a pharmacy customer will order a prescription refill in advance of his or her visit to the pharmacy to pick up the refill. Generally, the customer's order will then be filled, packaged, and stored until the customer visits the pharmacy to pick up the order. Many pharmacies store such an order in a common area along with other customers' orders that have also been placed in advance of those customers' visits to the pharmacy.

Upon arriving at the pharmacy, the customer generally proceeds to a point of sale area, such as a prescription pick-up window, and identifies himself or herself to a pharmacy technician or other on-duty employee. The pharmacy technician then locates and retrieves the customer's previously prepared order from the common storage area. In some cases, the pharmacy technician may ask the customer for further verification of his or her identity before the pharmacy technician retrieves the customer's order. Additionally, in some cases, the pharmacy technician and customer may review information about the customer's refill, and/or information about the customer's insurance coverage The customer may then pay for and receive the refill.

SUMMARY

In some embodiments, a method for advanced identification of a customer of a pharmacy includes receiving, at a first pharmacy computing device, identification information of the customer after an arrival of the customer at a pharmacy location associated with the first pharmacy computing device and before an arrival of the customer at a pharmacy pick-up area of the pharmacy location. The method also includes generating an identification of the customer based on the received identification information. The method further includes sending the identification of the customer to a second pharmacy computing device communicatively coupled to the first pharmacy computing device. The method further includes providing, using the second pharmacy computing device and based on the second pharmacy computing device receiving the identification of the customer, an indication to a pharmacy employee of the pharmacy location that the customer has arrived at the pharmacy location to pick up a previously prepared pharmacy order and that the pharmacy employee is to obtain the previously prepared pharmacy order for pick-up by the customer before the arrival of the customer at the pharmacy pick-up area.

In other embodiments, a system for advanced identification of a customer of a pharmacy includes at least one customer identification device located at the pharmacy and a computing device located at the pharmacy. The computing device is located remotely from the at least one customer identification device and is communicatively coupled to the at least one customer identification device. The at least one customer identification device is configured to receive identification information of the customer after an arrival of the customer at the pharmacy and before an arrival of the customer at a pick-up area of the pharmacy to pick up a previously prepared pharmacy order. The at least one customer identification device is also configured to generate an identification of the customer based on the received identification information. The computing device is configured to receive the identification of the customer from the at least one customer identification device. The computing device is also configured to generate an indication to an employee of the pharmacy, after receiving the identification of the customer from the at least one customer identification device and before the arrival of the customer at the pick-up area of the pharmacy, that the employee of the pharmacy is to obtain the previously prepared pharmacy order of the customer.

In yet other embodiments, a method for advanced identification of a customer of a pharmacy includes receiving, via at least one input device, identification information of the customer after an arrival of the customer at the pharmacy and before an arrival of the customer at an order pick-up area of the pharmacy. The method also includes determining an identity of the customer based on the received identification information. The method further includes using a computing device located remotely from the at least one input device to prompt an employee of the pharmacy to obtain an order of the customer from an order storage area of the pharmacy based on determining the identity of the customer. The method further includes prompting the customer to complete one or more aspects of a transaction for the order at least partially while the employee of the pharmacy obtains the order from the order storage area.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, whenever possible, the following description refers to the reference numerals included in the following figures, in which features depicted in multiple figures are designated with consistent reference numerals.

FIG. 5 illustrates an example customer information entry page, according to a still further embodiment;

DETAILED DESCRIPTION

The following text sets forth a detailed description of numerous different embodiments. However, it should be understood that the detailed description is to be construed as exemplary only and does not describe every possible embodiment since describing every possible embodiment would be impractical. One of ordinary skill in the art will recognize, in light of the teaching and disclosure herein, that numerous alternative embodiments could be implemented.

It should be understood that, unless a term is expressly defined in this patent application using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent application.

Figure 1:
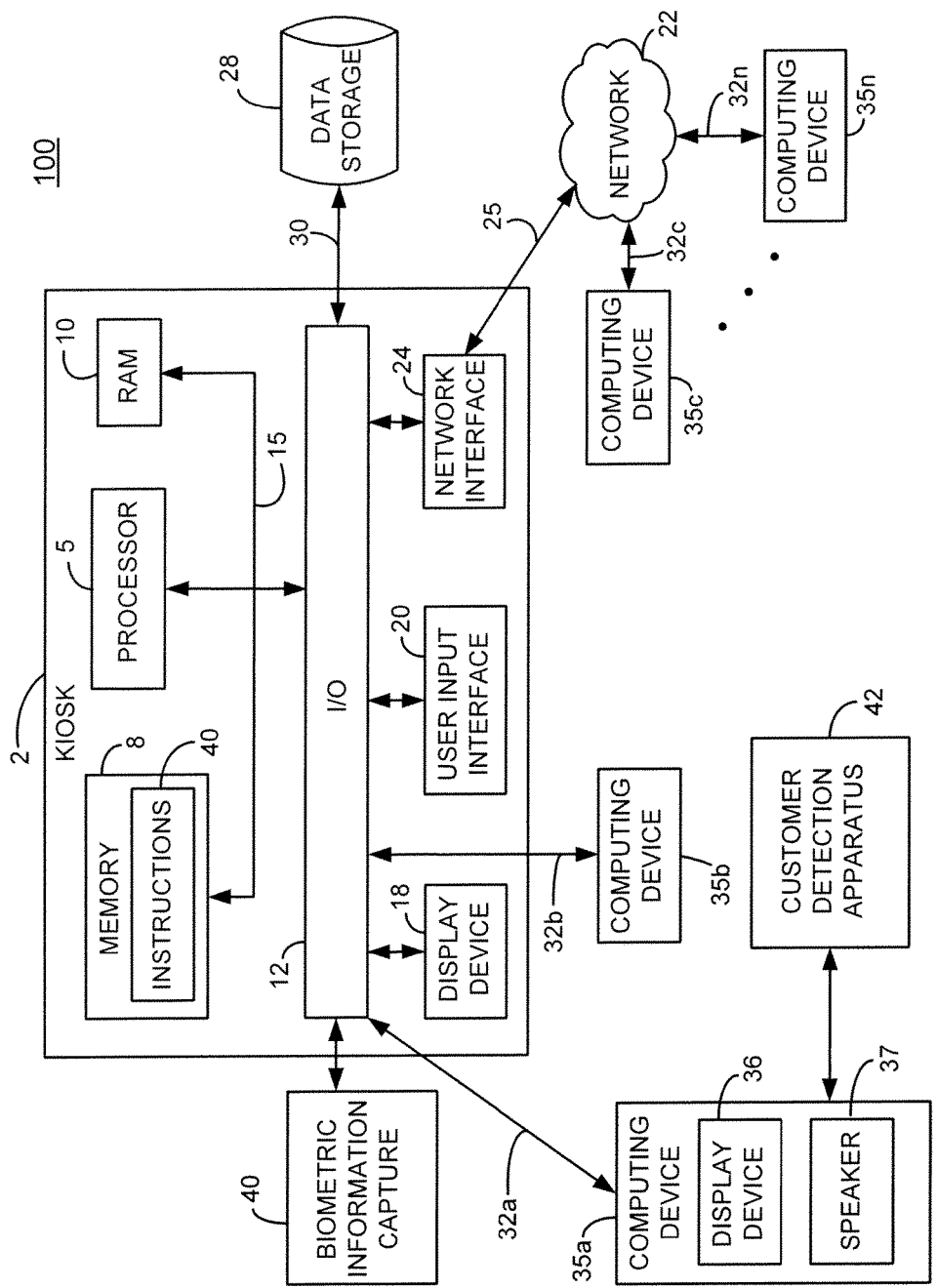
FIG. 1 is a block diagram of an example system for advanced identification of a customer of a pharmacy, according to an embodiment.

FIG. 1 is a block diagram of an example system 100 for advanced identification of a customer of a pharmacy, according to an embodiment of the present invention. In some embodiments, the system 100 may be implemented in at least a portion of a pharmacy computing system. As used herein, the term "pharmacy" may include a single outlet or a plurality of outlets affiliated with one or more entities that are licensed to dispense prescribed pharmaceutical products such as drugs, medicaments, durable medical equipment, or the like. The one or more entities may be located, by way of example rather than limitation, in separate geographic locations from each other, in different areas of the same city, or in different states. The pharmacy outlets may include, for example, one or more of a conventional retail store, space within a location operated by another commercial or not-for-profit entity (e.g., within a discount store, hospital, school, nursing home, etc.), an outlet in proximity with a warehouse or distribution center, a call-in pharmacy, a long-term care pharmacy, a workplace/on-site pharmacy, a specialty pharmacy, etc. The pharmacy may be commercial or not-for-profit, and may provide or vend other products in addition to the prescribed pharmaceutical products.

As used herein, the term "pharmacy computing system" may include a computing system that is owned and/or operated by a pharmacy to aid pharmacy employees and representatives to fill and dispense prescribed pharmaceutical products and other products. A pharmacy computing system may include at least one computing device, database, display device, and user input interface device. Typically, each outlet of a pharmacy may have a local instance of (or local access to) a pharmacy computing system. In some embodiments, local instances of a pharmacy computing system may be networked.

As used herein, the terms "customer", "pharmacy customer", or "patient" are interchangeable and may refer to a person who has been prescribed one or more pharmaceutical products such as drugs, medicaments, durable medical equipment, or the like. Additionally or alternatively, the interchangeable terms "pharmacy customer", "customer", or "patient" may refer to such person's representative. The representative may be, for example, a patient's caregiver or another suitable person who may interact with a pharmacy employee or pharmacy representative on behalf of a patient. Such interaction may occur in conjunction with a filling of or payment for a prescription order for the patient, including a refill order.

As used herein, the terms "pharmacy employee", "pharmacy representative", or "pharmacy technician" are interchangeable and may refer to a licensed pharmacist or a non-licensed pharmacy employee or pharmacy representative.

Generally, the system 100 may be used to provide a pharmacy employee with an advance identification of a customer who has arrived at the pharmacy to pick up a previously prepared pharmacy order. The previously prepared pharmacy order may be a refill of a prescription medication that the customer has called in ahead of time. Alternatively, the customer may have ordered the refill online, via text message, etc. With respect to the previously ordered refill, each of a drug utilization review, a drug interaction review, a confirmation of the customer's insurance coverage, a confirmation of the name and dosage of the medication, etc. may have already been performed by the time the customer arrives at the pharmacy to pick up the refill.

Advantageously, the system 100 may provide the advanced identification of the customer to the pharmacy technician shortly after an arrival of the customer at the pharmacy, and thereby allow the pharmacy technician to obtain the customer's previously prepared refill while the customer completes other aspects of his or her transaction for the refill. The refill may then be ready to be handed to the customer at a pharmacy pick-up area, such as a prescription pick-up window, immediately upon payment, without the customer having to unnecessarily wait for the pharmacy technician to find the refill. The indication that the customer has come to the pharmacy outlet to pick up his or her refill may be generated and provided to the pharmacy technician before an arrival of the customer at the pharmacy pick-up area or other point of sale. Example techniques for identifying the customer and providing the advance indication to the pharmacy technician, and examples of further advantages of one or more embodiments disclosed herein, are discussed further below.

The system 100 may include a plurality of computing devices associated with the pharmacy. For example, the system 100 may include a kiosk 2 located at the pharmacy, and may further include other computing devices 35a-35n, examples of which are described further below. In some embodiments, the kiosk 2 may function as a customer identification device that is used to provide the advance identification of the customer. In some embodiments, one or more of the user interface, functionality, size, shape, etc. of the kiosk 2 may resemble that of an automatic teller machine (ATM). The kiosk 2 may provide a variety of self-service options to the customer as further described below. Generally speaking, after providing identification information to the kiosk 2, the customer may use the kiosk 2 to complete certain aspects of a refill transaction while the pharmacy technician obtains the customer's refill. For the sake of illustration of one or more principles of the present disclosure, a simplified block diagram of the kiosk 2 is shown.

However, such principles may apply equally to other electronic devices, including, but not limited to, cellular telephones or other wireless devices, personal digital assistants, etc. The kiosk 2 may include a processor 5 (which may at times be referred to as a microcontroller or a microprocessor) for executing computer executable instructions, a program memory 8 for permanently storing data related to the computer executable instructions, a random-access memory (RAM) 10 for temporarily storing data related to the computer executable instructions, and an input/output (I/O) circuit 12, all of which may be interconnected via an address/data bus 15.

It should be appreciated that although only one processor 5 is shown, the kiosk 2 may include multiple processors 5. Similarly, the memory of the kiosk 2 may include multiple RAMs (Random Access Memories) 10 and multiple program memories 8. The RAMs 10 and program memories 8 may be implemented as semiconductor memories, magnetically readable memories, optically readable memories, and/or other tangible, non-transitory computer-readable storage media, for example. Additionally, although the I/O circuit 12 is shown as a single block, it should be appreciated that the I/O circuit 12 may include a number of different types of I/O circuits. For example, a first I/O circuit may correspond to a display device 18 of the kiosk 2, and the first or a second I/O circuit may correspond to a user input interface 20. The user input interface 20 may be, for example, a keyboard, a mouse, a touch screen, a voice activation device, or any other known user input interface device. In some embodiments, the display device 18 and the user input interface 20 may be jointly incorporated in a single physical device. The kiosk 2 may also include other elements common to general purpose computing devices.

The kiosk 2 may be operatively connected to a network 22 via a network interface 24 and a link 25. The network 22 may be a private network, a public network, or some combination of the two. The network 22 may be a client-server network, a peer-to-peer network, an Ethernet network, a cloud computing network, or any other known type of network in which computing devices are enabled to communicate. In some embodiments, the network 22 may include more than one network. The link 25 may be as simple as a memory access function or an Ethernet connection, and/or the link 25 may be a wired, wireless, or multi-stage connection. Many types of links are known in the art of networking and may be used in conjunction with the kiosk 2. In some embodiments, at least one of the display device 18 or the user input interface 20 may be remotely connected to the kiosk 2 using the network 22 and the link 25.

The processor 5 may be operatively connected to a database or storage entity 28 via a link 30. Similar to the link 25, the link 30 may be any type of link known in the art. In some embodiments, the link 30 may be the same link as the link 25, and the processor 5 may access the data store 28 via the network 22. In some embodiments, the data storage entity 28 may be contained within the kiosk 2. In some embodiments, the data storage entity 28 may be a plurality of databases or data storage entities.

The kiosk 2 may be in communicative connection with the computing devices 35*a*-35*n* via links 32*a*-32*n*. The computing devices 35*a*-35*n* may be located remotely from the kiosk 2. For example, the computing device 35*a* may be a computing device which is located at the same pharmacy outlet as the kiosk 2, but which is located in an area of the pharmacy outlet where the previously prepared pharmacy order is stored before the arrival of the customer at the pharmacy outlet. More particularly, the computing device 35*a* may be located in an area in which the identified customer's previously prepared pharmacy order is stored along with other customers' previously prepared pharmacy orders until such orders are to be picked up. In this manner, the computing device 35*a* may more readily provide information to the pharmacy technician working behind the prescription pick-up window, as further described below. The computing device 35*b* may, for example, correspond to a server for performing drug utilization review. The computing device 35*c* may, for example, be located at and/or associated with a different outlet of the pharmacy as compared to the kiosk 2 and the computing device 35*a*. The computing device 35*n* may, for example, provide access to data banks of patient or drug information. Similar to the links 25 and 30, each of the links 32*a*-32*n* may be any type of link known in the art, such as a direct link, wired, wireless, or other type of link. In some embodiments, the kiosk 2 may communicate with one or more of the computing devices (e.g., the computing devices 35*c* and 35*n*) via the network 22. Although not illustrated, the other computing devices 35*a*-35*n* may each also include elements typically found in general computing devices and similar to the kiosk 2, such as a memory, a processor, a RAM, a bus, a display, a user input interface, a network interface, and other elements.

The kiosk 2 may include one or more sets of computer executable instructions 40 for performing advanced identification of a pharmacy customer, according to various embodiments. As used herein, the terms "computer-executable instructions," "computer executable instructions," and "instructions" are interchangeable. The instructions 40 may be stored in the memory 8 and executable by the processor 5 to generate, for example, the advanced identification of the customer that will be provided to the pharmacy technician.

Figure 2:
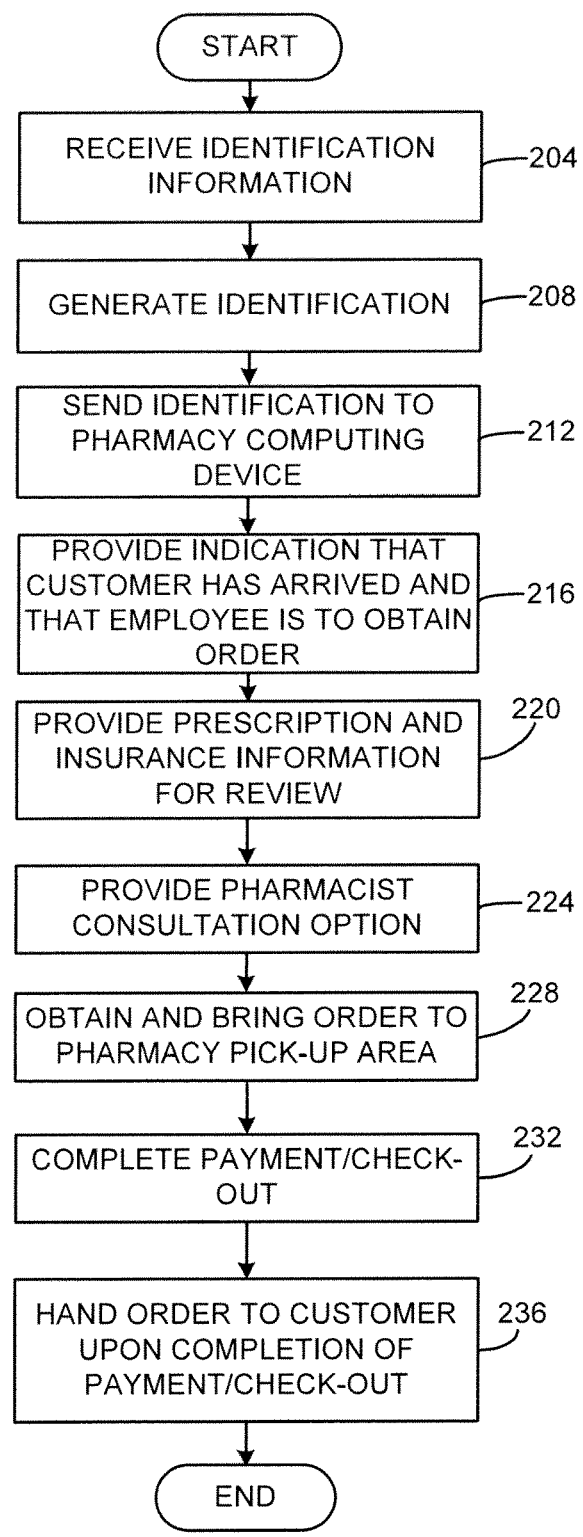
FIG. 2 is a flow chart showing an example method for performing advanced identification of a pharmacy customer, according to another embodiment.

FIG. 2 is a flow chart showing an example method 200 for performing advanced identification of a pharmacy customer, according to an embodiment. For ease of explanation, the method 200 will be described with reference to the system 100 of FIG. 1. However, it will be understood that the method 200 may be implemented by a system other than the system 100. Similarly, it will be understood that the system 100 may implement methods other than, or in addition to, the method 200.

At blocks 204 and 208, identification information of the customer may be received and an identification of the customer may be generated based on the received identification information. In some embodiments, the identification information may be received at the kiosk 2. The kiosk 2 may be located in any suitable portion of the pharmacy outlet, such as at or near a pharmacy counter or other point of sale area, i.e., a portion of the pharmacy outlet at which prescribed pharmaceutical products are dispensed. In some embodiments, the kiosk 2 may be located near the entrance to the pharmacy outlet to encourage customers to use the pharmacy outlet's advanced customer identification offering.

In some embodiments, the pharmacy outlet may include multiple ones of the kiosk 2 to allow advance identification of multiple customers at the same time. Each of the multiple kiosks may be located in any suitable portion of the pharmacy. For example, in various embodiments, each of the multiple kiosks may be located at or near the prescription pick-up window or point of sale area; each of the multiple kiosks may be located at or near the entrance to the pharmacy; one or more of the multiple kiosks may be located at and/or near the prescription pick-up window while one or more other ones of the multiple kiosks may be located at and/or near the entrance to the pharmacy; or the multiple kiosks may be distributed in any other desired manner among any one or more desired locations at the pharmacy outlet.

In some embodiments, the customer may be picking up a prescription refill. In other embodiments, the customer may additionally or alternatively be picking up a prescribed pharmaceutical product which is not a refill, including, for example, an initial supply of a prescribed pharmaceutical product which the customer has not used before. The prescription for the initial supply may, for example, have already been called in by the customer's doctor.

Figure 3A:
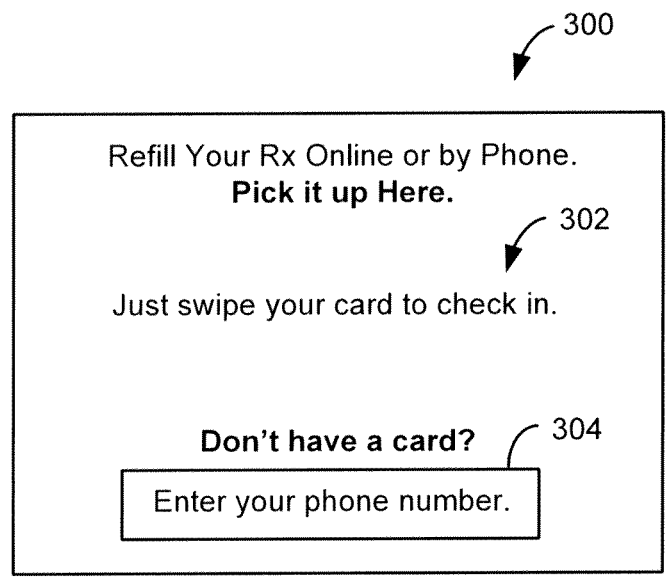
FIG. 3A illustrates an example kiosk welcome page, according to yet another embodiment.

The identification information received at block 204 may be any suitable information which may be used to indicate to a pharmacy technician that the customer is present at the pharmacy and that the pharmacy technician should obtain the customer's refill and bring the refill to the prescription pick-up window. For example, when the customer approaches the kiosk 2, the kiosk 2 may prompt the customer to use at least one input device of the kiosk 2, and/or at least one input device communicatively coupled to the kiosk 2, to provide suitable personal information in order to identify himself or herself. For example, FIG. 3A is a screen shot of a kiosk welcome page 300 which the kiosk 2 may, for example, be configured to display when the customer first approaches the kiosk 2. The kiosk welcome page 300 may display, among other features, a card-based identification option 302 and a telephone number identification option 304.

The card-based identification option 302 may, in one embodiment, be a message inviting the customer to swipe a card issued by a party distinct from the pharmacy but that nevertheless identifies the customer to the kiosk 2. For example, the pharmacy may have information on file that identifies a debit card or credit card of which the customer is an authorized user. Thus, in an embodiment, the customer may swipe his or her debit card or credit card using a magnetic card reader (not shown) communicatively coupled to the processor 5. The processor 5 may process signals received from the magnetic card reader in conjunction with the pharmacy's stored card information for various customers. For example, the stored card information may include card information of the customer who has just swiped his or her debit card or credit card and card information of at least one additional customer of the pharmacy. For example, the processor 5 may access the stored card information via the computing device 35*n*, which may, in an embodiment, provide access to one or more data banks in which the card information is stored. The signals from the magnetic card reader may be indicative of the customer's card number, and the processor 5 may thus generate the identification of the customer at block 208 by comparing the signals from the magnetic card reader to the stored card information.

In various other embodiments, the customer may respond to the card-based identification option 302 by swiping a card issued by the pharmacy which identifies the customer to the kiosk 2. The card issued by the pharmacy may be, for example, a credit card issued by the pharmacy, a discount or rewards card that the customer may use to gain access to certain savings and offerings, or any other suitable card that identifies the customer to the pharmacy. Of course, the card issued by the pharmacy may instead be a card issued for the specific purpose of performing advance identification of the customer when the customer is picking up a previously prepared refill or other pharmacy order, according to an embodiment. In any event, the processor 5 may access corresponding stored card information for various customers, such as in the manner described above, and may generate the identification of the customer based on, for example, a comparison of the stored card information to signals from the magnetic card reader that are indicative of the customer's card number.

In further embodiments, the customer may respond to the card-based identification option 302 by using a bar code reader (not shown) communicatively coupled to the processor 5 to scan a pharmacy-issued card having a bar code printed thereon. The bar code reader may obtain a signal indicative of the bar code on the pharmacy-issued card, and this signal may allow the processor 5 to generate the identification of the customer in a similar manner that the processor 5 may generate the identification of the customer based on unique card information, as described above.

Of course, the customer may respond to the card-based identification option 302 issued by the pharmacy in a number of other suitable ways. As just one example, the customer may respond to the card-based identification option 302 by allowing a radio-frequency identification (RFID) terminal communicatively coupled to the processor 5 to detect an RFID tag issued to the customer by the pharmacy. For example, the RFID tag may be included within a card that the pharmacy has issued to the customer. In one example, as will be understood by one of ordinary skill in the art in light of the teaching and disclosure herein, the customer may allow the RFID terminal to detect the RFID tag by placing his or her card including the RFID tag at a sufficiently close proximity to the RFID terminal. Of course, the RFID tag may also be included within any other device suitable for use in identifying the customer to the pharmacy.

Figure 4:
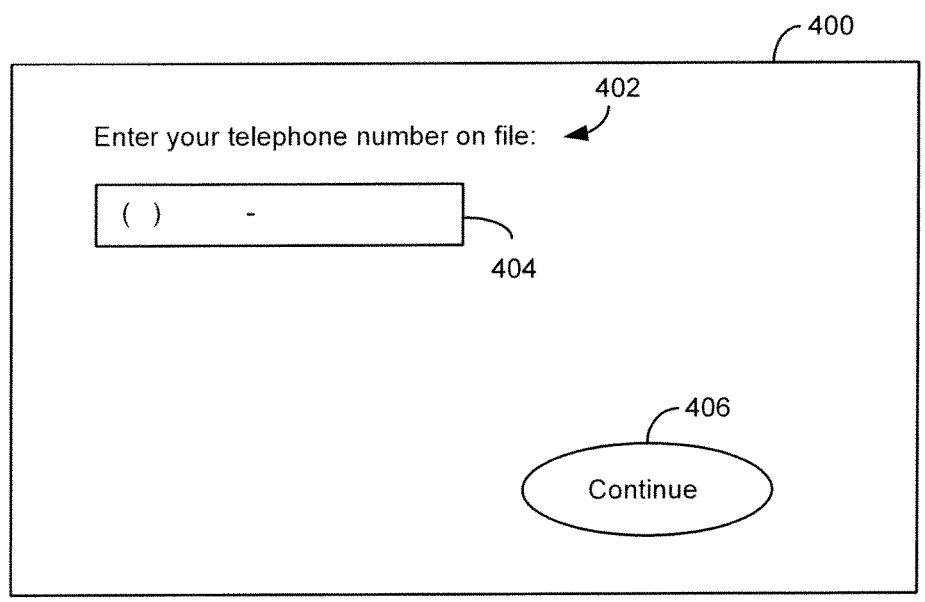
FIG. 4 illustrates an example telephone number entry page, according to yet a further embodiment.

Alternatively, the customer may prefer not to identify himself or herself to the kiosk 2 using a card-based method, and/or may not have access to any card that identifies him or her to the kiosk 2. Accordingly, the kiosk 2 may provide one or more other suitable options for the customer to supply identification information. As just one example, the customer may use the telephone number identification option 304 to supply a telephone number that the pharmacy has on file. In one embodiment, the user input interface 20 includes a mouse, and the telephone number identification option 304 is an option on the kiosk welcome page 300 which the customer may select with an appropriate click of the mouse. For example, the telephone number identification option 304 may include a clickable button, which may in turn include a textual message such as "Enter your phone number". Upon clicking the button, the customer may be directed to a telephone number entry page 400, one example of which is shown in FIG. 4.

The telephone number entry page 400 may include a message 402 instructing the customer to enter his or her telephone number on file with the pharmacy into a telephone number entry field 404, according to an embodiment. The customer may enter his or her telephone number and then select a button 406 which may be labeled "Continue", for example. The processor 5 may thereupon access stored telephone number information for various customers, such as by accessing one or more corresponding data banks via the computing device 35*n*. Based on a comparison of the customer's entered telephone number to the stored telephone number information, the processor 5 may generate the identification of the customer.

Figure 3B:
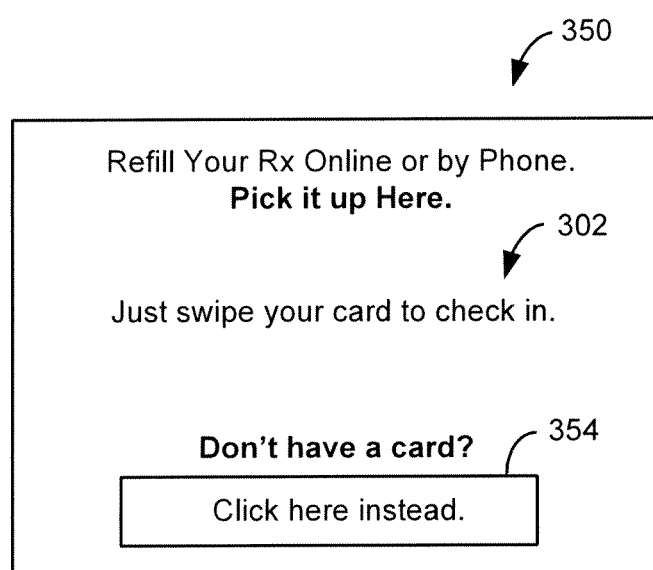
FIG. 3B illustrates an alternative kiosk welcome page, according to still another embodiment.

Of course, information other than the customer's telephone number may be received at block 204 in order to generate the identification of the customer at block 208. In just one example, an alternative kiosk welcome page 350, such as that shown in FIG. 3B, may include a more general alternative identification option 354 instead of the telephone number identification option 304. The alternative identification option 354 may also include a clickable button, which may display a textual message such as "Click here instead". If the customer clicks on the alternative identification option 354, he or she may then be directed to a customer information entry page 500, one example of which is shown in FIG. 5, to enter other personal information.

The customer information entry page 500 may include a message 502 instructing the customer to enter personal information using another portion of the customer information entry page 500, such as one or more personal information fields below the message 502. As shown in FIG. 5, the personal information fields may include, for example, one or more of a last name field 504, a first name field 506, a home address field 508, a prescription number field 510, and a date of birth field 512. Of course, other suitable personal information fields could be included on the customer information entry page 500 instead of or in addition to any of the fields 504-512.

As the customer enters his or her personal information into the one or more personal information fields, the processor 5 may compare the entered information to corresponding stored information for various customers. For example, the pharmacy may have access to one or more data banks storing the last names of all customers of the pharmacy. In an embodiment, the customer may enter his or her last name into the last name field 504. The processor 5 may then identify the customer, or at least narrow down the possible identities of the customer, by comparing the entered last name with the last names stored in the one or more data banks. In some embodiments, if the processor 5 is unable to identify the customer based on his or her last name (or other suitable personal information), the processor 5 may cause the display device 18 to display a prompt to the customer to enter more personal information into other ones of the personal information fields. In some embodiments, the processor 5 may determine that it is unable to identify the customer, and may therefore display such a prompt, in response to the customer attempting to proceed beyond the customer information entry page 500, such as by selecting a button 514 labeled "Continue".

In some embodiments, after the customer has provided sufficient personal information to identify himself or herself, the processor 5 may generate the identification of the customer accordingly. The kiosk 2 may then display a message, on the customer information entry page 500 or elsewhere, stating that the customer's identity has been determined, and/or informing the customer of his or her determined identity and requesting confirmation thereof. The customer may select a suitable option (e.g., by clicking a suitable button) to acknowledge this message and/or confirm his or her identity. In some embodiments, the identification of the customer may not be generated, and such a message may not be displayed, until the customer selects, for example, the button 514.

In some embodiments where more than one personal information field is displayed on the customer information entry page 500, the customer may be required to fill in all of the displayed personal information fields in order to select the button 514 or otherwise proceed beyond the customer information entry page 500, even though the processor 5 may generate the identification of the customer after the customer fills in fewer than all of the personal information fields. In one such embodiment, the kiosk 2 may display the aforementioned message prompting the customer to acknowledge and/or confirm his or her identity, and after the customer responds to the message, the customer information entry page 500 may remain on the screen or the kiosk 2 for the customer to continue entering the rest of his or her personal information. Upon completing the entry of all personal information, the customer may, for example, select the button 514.

If, after the customer selects the button 514, the processor 5 determines that any of the additional personal information that the customer fills in does not match the generated identification of the customer, the processor 5 may override its previously generated identification of the customer. More specifically, the processor 5 may have sent the previously generated identification of the customer to the computing device 35a, as further described below. This identification may have caused a corresponding indication of the customer's identity to be provided to the pharmacy technician, as still further described below. However, if the processor 5 overrides its previously generated identification of the customer, the processor 5 may generate and send (not shown) a signal to the computing device 35a in order to cancel the corresponding indication of the customer's identity that was previously provided to the pharmacy technician.

In yet another embodiment, the customer information entry page 500 may display a limited number of personal information fields which the processor 5 may use to generate the identification of the customer. After the processor 5 generates the identification of the customer, the customer may select the button 514 in order to confirm the generated identification, at which time the customer may be required to fill in additional personal information fields on another page.

Of course, the customer information entry page 500 may be implemented in any of a number of other suitable ways, in addition to the various examples set forth herein.

In still another embodiment, if the customer selects the alternative identification option 354 on the alternative kiosk welcome page 350, the kiosk 2 may prompt the customer to provide one or more pieces of his or her biometric information to the kiosk 2 using a biometric information capture apparatus 40. In some embodiments, the biometric information capture apparatus 40 may function as a customer identification device that is communicatively coupled to the kiosk 2, as shown in FIG. 1.

According to an embodiment, the biometric information capture apparatus 40 may be or may include a fingerprint reader (not shown). The pharmacy may maintain stored fingerprint information for various customers who have opted to provide such information in order to avail themselves of the pharmacy's advanced customer identification offering. For example, the stored fingerprint information may be maintained in one or more data banks, such as one or more data banks which the kiosk 2 may access via the network 22 and the computing device 35n. After arriving at the pharmacy to pick up a refill, the customer may provide his or her fingerprint information to the biometric information capture apparatus 40 by, for example, sliding his or her index finger over the fingerprint reader. The processor 5 may process signals received from the fingerprint reader and, at block 208, may generate the identification of the customer based on a comparison of such signals with the stored fingerprint information.

According to another embodiment, the biometric information capture apparatus 40 may include or may be an iris scanner (not shown) in addition to or instead of the fingerprint reader. The pharmacy may maintain stored iris information for various customers who have opted to provide such information in order to avail themselves of the pharmacy's advanced customer identification offering. For example, for each of the various customers, the stored iris information may include a coded representation of the customer's iris as derived from a previously-captured image(s) of the customer's iris. For example, each customer who opts to use iris scanning for authentication purposes may have previously agreed to an iris scan, during which the pharmacy may have captured the image of the customer's iris necessary to generate and store the coded representation thereof. The coded representation and/or other iris information may be maintained in one or more data banks, such as one or more data banks which the kiosk 2 may access via the network 22 and the computing device 35n. After arriving at the pharmacy to pick up a refill, the customer may provide his or her iris information to the biometric information capture apparatus 40 by, for example, placing his or her eye in front of the iris scanner. The processor 5 may receive a coded representation of the customer's iris from the iris scanner and, at block 208, may generate the identification of the customer based on a comparison of this coded representation with the stored coded representations for the various customers.

According to yet another embodiment, the biometric information capture apparatus 40 may include or may be an ear imaging device or devices (not shown) in addition to or instead of the fingerprint reader and/or the iris scanner. The pharmacy may maintain stored ear shape information for various customers who have opted to provide such information in order to avail themselves of the pharmacy's advanced customer identification offering. For example, for each of the various customers, the stored ear shape information may include a coded representation of the customer's ear shape as derived from a previously-captured image(s) of the customer's ear shape. For example, each customer who opts to use ear recognition for authentication purposes may have previously agreed to imaging of his or her ear. During such previous imaging, the pharmacy may have captured the data necessary to generate and store the coded representation of the customer's ear shape. The coded representation and/or other ear shape information may be maintained in one or more data banks, such as one or more data banks which the kiosk 2 may access via the network 22 and the computing device 35n. After arriving at the pharmacy to pick up a refill, the customer may provide his or her ear shape information to the biometric information capture apparatus 40 by, for example, placing his or her ear in front of the ear imaging device for imaging of his or her ear. The processor 5 may receive a coded representation of the customer's ear shape from the ear imaging device and, at block 208, may generate the identification of the customer based on a comparison of this coded representation with the stored coded representations for the various customers.

According to still another embodiment, the biometric information capture apparatus 40 may include or may be a facial recognition device or devices (not shown), in addition to or instead of the fingerprint reader and/or the iris scanner and/or the ear imaging device(s). The pharmacy may maintain stored facial profile information for various customers. For example, for each of the various customers, the stored facial profile information may include a coded representation of various features of the customer's face, such as eye, nose, cheekbones, or jaw; the position of such features relative to one another; or the like. The facial profile information may also or alternatively include, for example, a coded representation of the shape of the customer's face. The pharmacy may have previously gathered the customer's facial profile information using, for example, one or more monitoring devices that the pharmacy uses for the specific purpose of allowing advanced customer identification, or from one or more monitoring devices that the pharmacy uses as part of its customary operations, such as a security camera. In another embodiment, the customer may have previously allowed the pharmacy to gather his or her facial profile information. For example, the customer may have consented to appropriate imaging of his or her face during a previous visit to the pharmacy, such as a visit for the purpose of setting up the customer's participation in the advanced customer identification offering. More generally, in some embodiments, the pharmacy may have previously gathered the facial profile information for the customer from, for example, a photograph that the customer has made physically or electronically available to the pharmacy, such as via the Internet.

The customer's facial profile information may be maintained in one or more data banks, such as one or more data banks which the kiosk 2 may access via the network 22 and the computing device 35n. After arriving at the pharmacy to pick up a refill, the customer may provide his or her facial profile information to the biometric information capture apparatus 40 by, for example, allowing appropriate imaging of his or her face by the facial recognition device (e.g., a digital camera). The processor 5 may receive the customer's facial profile information from the facial recognition device and, at block 208, may generate the identification of the customer based on a comparison of this facial profile information with the stored facial profile information for the various customers.

Of course, one of ordinary skill in the art will recognize numerous other ways in which the identification information of the customer may be received at block 204 and/or numerous other ways in which the identification of the customer may be generated at block 208, including other suitable ways of using biometric information, using other identification information that the customer may input to the kiosk, etc. Additionally, the identification of the customer need not be generated by the kiosk 2. Instead, one of ordinary skill in the art will recognize, in light of the teaching and disclosure herein, that the identification of the customer could be generated at block 208 by another device in the system 100 which may be communicatively coupled to the kiosk 2. For example, another one of the computing devices 35a-35n, such as the computing device 35c, may function as a further customer identification device that generates the identification of the customer at block 208 based on the identification information received at the kiosk 2 at block 204. In this example, the computing device 35c may then send the identification of the customer to the computing device 35a at block 212, via the network 22, for use by the computing device 35a as further described below. Additionally, when the customer uses the biometric information capture apparatus 40, the biometric information capture apparatus 40 may generate the identification of the customer and communicate this identification to the kiosk 2, in some embodiments.

With continued reference to FIG. 2, at block 212, the processor 5 may send an identification of the customer to a pharmacy computing device. For example, the computing device 35a may be positioned behind the prescription pick-up window in an area where previously prepared pharmacy orders for multiple customers are kept until paid for and picked up. Accordingly, the processor 5 may send the identification of the customer to the computing device 35*a* via the link 32*a*.

Upon receiving the identification of the customer, the computing device 35*a* may provide a corresponding indication to the pharmacy technician at block 216, such as by using an I/O device to output a visual alert. For example, in some embodiments, the computing device 35*a* may provide the indication to the pharmacy technician by using a display device 36 of the computing device 35*a* to output a visual alert indicating that the identified customer has arrived at the pharmacy to pick up his or her previously prepared pharmacy order (e.g., a refill order). In any event, the indication provided to the pharmacy technician at block 216 may indicate that the pharmacy technician is to obtain the previously prepared pharmacy order for pick-up by the customer before the arrival of the customer at the pharmacy pick-up area. In this manner, the previously prepared pharmacy order may be ready for pick-up by the customer upon payment for the previously prepared pharmacy order, in some embodiments.

Figure 6:
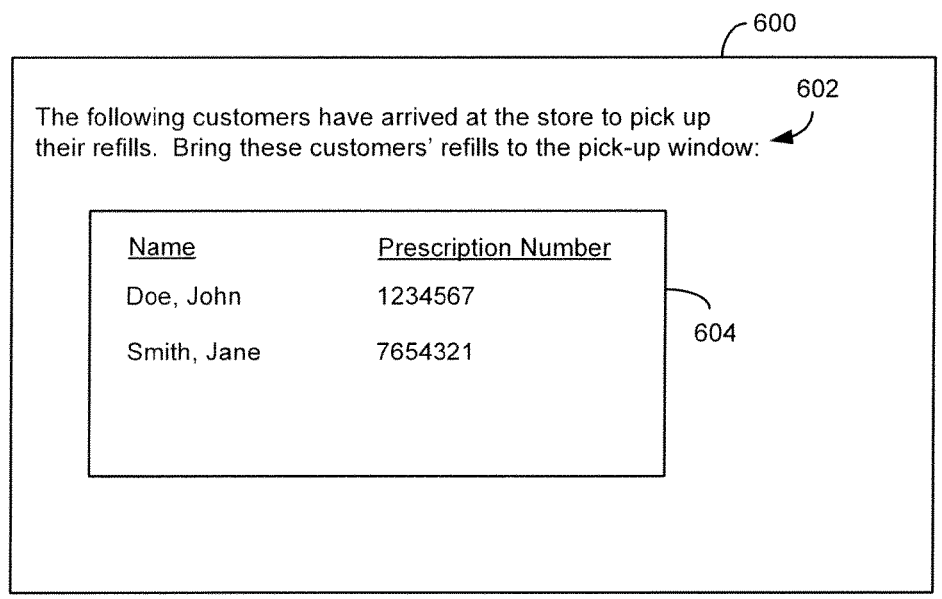
FIG. 6 illustrates an example order pickup screen, according to yet another embodiment.

For example, FIG. 6 illustrates an example order pickup screen 600 that may be displayed on the display device 36. The order pickup screen 600 includes a general message 602 indicating that the order pickup screen 600 lists customers who have arrived at the pharmacy to pick up their pharmacy orders. The order pickup screen 600 further includes a customer identification field 604, which may list one or more individual customers who have been determined (e.g., at block 204) to have arrived at the pharmacy and whose previously prepared pharmacy orders the pharmacy technician is to obtain before an arrival of each customer at the pharmacy pick-up area. The customer identification field 604 may include any suitable information to assist the pharmacy technician in quickly determining which customer's pharmacy order to obtain. For example, the customer identification field 604 may include one or more of the name of the customer, the customer's prescription number, etc., as shown in FIG. 6.

Of course, the indication may be displayed or otherwise provided to the pharmacy technician at block 216 in many suitable ways. For example, the computing device 35*a* itself may be kept in a separate area of the pharmacy, or may even be located off-site from the particular pharmacy outlet, and hence may not be accessible to the pharmacy technician. However, in this example, the display device 36 may be implemented remotely from, and communicatively coupled to, a processor of the computing device 35*a* in any suitable manner, such as via a direct link or, for example, via the network 22 and the link 25. The display device 36 and any visual alert output therefrom may then be viewable by the pharmacy technician. For example, the display device 36 may be a television monitor, which may be mounted to a wall in order to increase the visibility of the display device 36 to the pharmacy technician from relatively long distances within the area behind the prescription pick-up window.

In some embodiments, the computing device 35*a* may also or alternatively provide the indication to the pharmacy technician, such as by using an I/O device to output an audible alert. For example, in some embodiments, the computing device 35*a* may provide the indication to the pharmacy technician at block 216 by using a speaker 37 of the computing device 35*a* to output an audible alert that generally informs the pharmacy technician that a customer has identified himself or herself using the system 100. For example, when the processor 5 generates the indication of the identity of the customer, the processor 5 may also generate an audio signal that is then provided to the speaker 37. Moreover, in some embodiments, the speaker 37 may not be a component of the computing device 35*a*. The speaker 37 may instead be a stand-alone speaker that may be communicatively coupled to the kiosk 2 in any desired manner, such as in one of the manners described above. In some embodiments where the speaker 37 provides the audible alert, the display device 36 may further display the order pickup screen 600. Upon hearing the audible alert, the pharmacy technician may view the order pickup screen 600 to determine the identity of the customer and thus obtain that customer's order.

A general indication of a customer's arrival at the pharmacy to pick up a pharmacy order may be provided in other suitable ways as well. For example, in addition to or instead of using the speaker 37 as described above, a visual alert such as a blinking light on the computing device 35*a*, a blinking stand-alone light, etc., may be activated in a manner similar to the manner in which the audible alert may be provided via the speaker 37.

Generally speaking, in some embodiments, the customer may be prompted to complete one or more aspects of a transaction for the previously prepared pharmacy order at least partially while the pharmacy technician obtains the previously prepared pharmacy order from the area in which the previously prepared pharmacy order is stored along with other customers' previously prepared pharmacy orders. For example, with reference still to FIG. 2, at block 220, the kiosk 2 may provide, using the display device 18, information regarding the previously prepared pharmacy order to the customer for review by the customer before the customer proceeds to the pharmacy pick-up area. In this manner, by using the computing device 35*a* to provide the aforementioned indication to the pharmacy technician when the computing device 35*a* receives the identification of the customer, the indication is provided to the pharmacy technician so that the pharmacy technician is to obtain the previously prepared pharmacy order of the customer at least partially while the customer reviews the information regarding the previously prepared pharmacy order, in some embodiments. While the pharmacy technician is obtaining the customer's order, the customer may review any suitable information regarding his or her previously prepared pharmacy order the accuracy of which is needed or desired to be confirmed. For example, the kiosk 2 may display, in some embodiments, one or both of prescription information and insurance information regarding the previously prepared pharmacy order for review by the customer.

More particularly, in some embodiments, the kiosk 2 may display one or more of the name of the product(s) included in the previously prepared pharmacy order, the number of doses included in the previously prepared pharmacy order, the prescribing doctor, the number of refill(s) the customer has left, general information about a product(s) included in the previously prepared pharmacy order, or the like. The kiosk 2 may also or alternatively display, in some embodiments, one or more of a name of the customer's insurance provider, a policy number of the customer's insurance policy, a group number associated with the customer's insurance policy, an amount of a deductible associated with the customer's insurance policy, an amount of a co-payment associated with the customer's insurance policy, any special messages such as a notification that the customer's insurance provider refused to provide coverage for the refill or other type of previously prepared pharmacy order, or the like. The kiosk 2 may provide the customer with one or both of an option to confirm that the provided information regarding the previously prepared pharmacy order is accurate or an option for the customer to dispute at least some of the information regarding the previously prepared pharmacy order. If the customer disputes any of the information displayed at block 220, he or she may take any suitable action. For example, the kiosk 2 may allow the customer to terminate the kiosk transaction and proceed directly to the prescription pick-up window to discuss his or her concerns with the pharmacy technician or, in some cases, another on-duty pharmacy employee, or both. The kiosk 2 may also, at block 224, provide the customer with the option of scheduling a consultation with an on-duty pharmacist.

Figure 7:
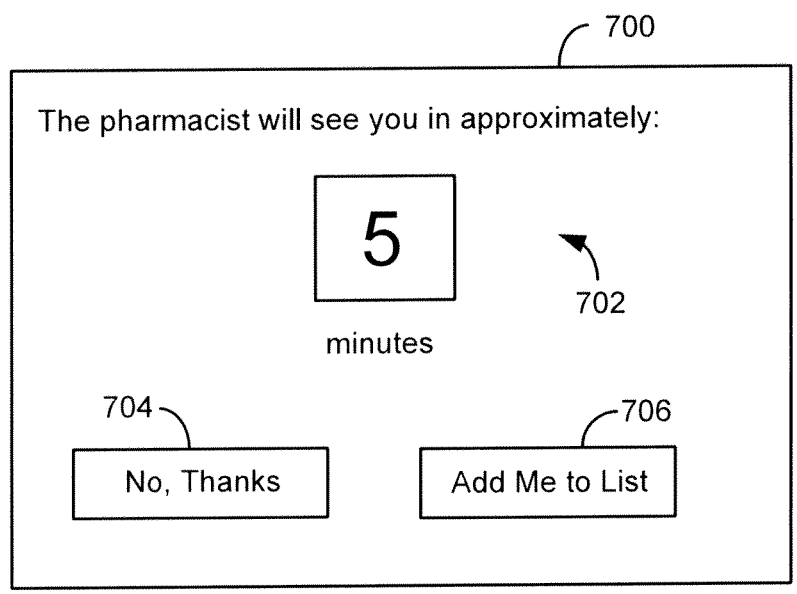
FIG. 7 illustrates an example of pharmacist consultation information, according to still another embodiment.

More specifically, at block 224, the kiosk 2 may provide the pharmacist consultation option by displaying pharmacist consultation information 700, such as that shown in FIG. 7. The pharmacist consultation information 700 may include an indication 702 of an estimated wait time for the customer to see an on-duty pharmacist, a consultation decline option 704, and a consultation accept option 706. In some embodiments, the pharmacist consultation information 700 may be displayed simultaneously with the customer's prescription and insurance information on a suitable portion of the display device 18. In other embodiments, the pharmacist consultation information 700 may be displayed as a separate image or "page". In any event, by using the kiosk 2 to provide the pharmacist consultation information 700 to the customer before the customer proceeds to the pharmacy pick-up area, and using the computing device 35a to provide the aforementioned indication to the pharmacy technician, the indication is provided to the pharmacy technician so that the pharmacy technician is to obtain the previously prepared pharmacy order of the customer at least partially while the customer selects one of the consultation accept option 706 or the consultation decline option 704, in some embodiments.

The indication 702, as shown in FIG. 7, may be a simple graphical element that shows the expected wait time for the customer as determined, for example, based on the number of on-duty pharmacists, the number of other customers who have already scheduled pharmacist consultations, and so on. Upon viewing the indication 702 of his or her estimated wait time, the customer may decline or accept a pharmacist consultation. According to an embodiment, each of the consultation decline option 704 and the consultation accept option 706 are clickable buttons on the screen of the display device 18, and the customer may decline or accept the pharmacist consultation by clicking the button that corresponds to his or her choice.

Of course, the customer may select the consultation accept option 706 to schedule a pharmacist consultation for any desired reason, even if the customer does not have any concerns regarding his or her prescription or insurance information. For example, the customer may select the consultation accept option 706 in order to ask an on-duty pharmacist a general health question, to request a recommendation from the on-duty pharmacist for an over-the-counter drug, etc. Additionally, in some embodiments, the pharmacist may be the sole person working at the prescription pick-up area, and thus may perform both the duties that are generally described herein as being performed by the pharmacy technician and additional duties such as, for example, conducting scheduled consultations with customers.

At block 228, the pharmacy technician may obtain the customer's previously prepared pharmacy order (e.g., a prescription refill) and bring this order to the pharmacy pick-up area.

It should be understood that various features of the method 200 are described with respect to distinct blocks for ease of explanation. However, one or more features of the method 200 may be performed at the same time, or at least during overlapping times. For example, at least a portion of block 228 may be performed while at least a portion of block 220 and/or block 224 are performed. Thus, the pharmacy technician may advantageously obtain and bring the customer's refill to the prescription pick-up window at block 228 at least partially while the customer uses the kiosk 2 to verify his or her prescription or insurance information at block 220, and/or at least partially while the customer reviews the pharmacist consultation information 700 and accepts or declines a pharmacist consultation at block 224. Accordingly, it will be understood that the particular placement of block 228 in the example of FIG. 2 is by way of example and illustration, and not by way of limitation.

Figure 8A:
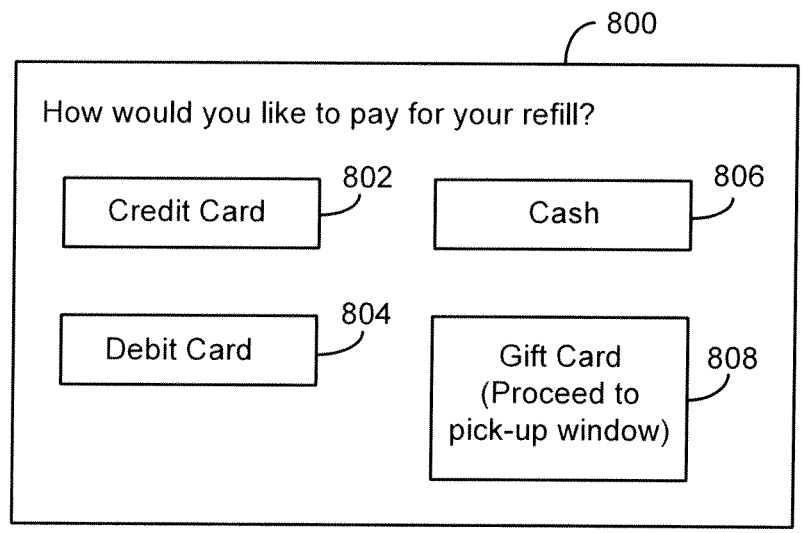
FIG. 8A illustrates an example payment page, according to another embodiment.

At block 232, the kiosk 2 may be used to complete the check-out process. For example, the kiosk 2 may display a payment page 800 as shown in FIG. 8A. The payment page 800 may display one or more options for the customer to pay for the previously prepared pharmacy order before the customer proceeds to the pharmacy pick-up area. For example, the payment page 800 may display an option 802 for the customer to pay for his or her refill using a credit card, an option 804 for the customer to pay with a debit card, an option 806 for the customer to pay with cash, or another similar option(s) for another suitable method(s) of payment that may be supported by the kiosk 2. When the customer selects one of the payment options provided by the kiosk 2, the kiosk 2 may provide a suitable interface for the customer to complete payment accordingly. For example, if the customer selects one of the payment options 802 or 804, the kiosk 2 may provide an option for the customer to use a magnetic card reader (not shown) communicatively coupled to the kiosk 2 to perform a payment process. In any event, it will be appreciated that in some embodiments, by using the computing device 35a to provide the aforementioned indication to the pharmacy technician that the customer has arrived at the pharmacy, the indication is provided to the pharmacy technician so that the pharmacy technician is to obtain the previously prepared pharmacy order of the customer at least partially while the customer pays for the previously prepared pharmacy order via the kiosk 2. Once the customer completes payment at the kiosk 2, the kiosk 2 may terminate the current session with the customer.

In some embodiments, the kiosk 2 may not support a certain method(s) of payment, and may display an option 808 for such a method, such as an option to pay using a gift card, as shown in FIG. 8A. In other words, the gift card may be valid at the pharmacy, but the kiosk 2 may not be capable of processing a payment made using the gift card. Additionally or alternatively, the option 808 or another option may be a more general option for the customer to pay for the previously prepared pharmacy order at the pharmacy pick-up area instead of via the kiosk 2. For example, the option 808 or another option may be labeled with a general indication such as "Other payment method" and/or a general indication such as "I'd like to pay at the counter". When the customer selects the option 808, the kiosk 2 may terminate the current session with the customer. In still other embodiments, the kiosk 2 may not support any methods of payment, and may therefore terminate the current session with the customer after, for example, the customer accepts or declines a pharmacist consultation at block 224.

Figure 8B:
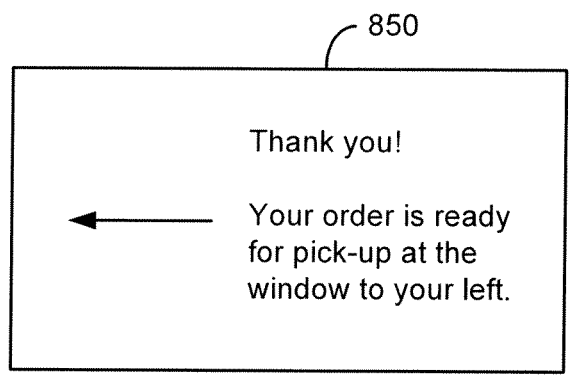
FIG. 8B illustrates an example kiosk session concluding page, according to yet another embodiment.

In any event, when the kiosk 2 terminates the session with the customer, the kiosk 2 may display a suitable message instructing the customer to pick up his or her refill from the pharmacy pick-up area. FIG. 8B shows an example concluding page 850, which thanks the customer for using the pharmacy's advanced customer identification service and directs the customer to the pharmacy pick-up area.

Once the customer's session at the kiosk 2 is completed, he or she may proceed to the prescription pick-up window. If the check-out/payment process still needs to be completed after the customer's session at the kiosk 2 is completed, the pharmacy technician or other employee at the prescription pick-up window may complete the payment process with the customer.

Of course, it will be appreciated in view of the foregoing disclosure that at least a portion of block 232 may be performed while at least a portion of block 228 is performed. Additionally, at least in view of the disclosure with respect to block 228, it will further be appreciated that the method 200 allows the customer's previously prepared pharmacy order to advantageously be ready for pick-up by the customer as soon as he or she completes the payment process. Moreover, the method 200 may advantageously allow the customer to identify himself or herself, review prescription and insurance information, accept or decline a pharmacist consultation, and complete the payment process with, in some embodiments, only a swipe of a card and several mouse clicks at the kiosk 2. Accordingly, at block 236, the customer's previously prepared pharmacy order may be handed to him or her upon completion of the check-out process without unnecessarily prolonging the check-out process, without the customer having to wait for the pharmacy technician to obtain his or her order after the check-out process has already been completed, etc.

After block 236, the method 200 may end, and the method 200 may be repeated as needed or desired.

While various examples of the method 200 for advanced identification of a pharmacy customer have been shown and described above, many variations of the example method will be recognized by one of ordinary skill in the art in light of the teaching and disclosure herein. As explained above, the various blocks of the method 200 need not be performed at distinct times and in some cases may even be performed simultaneously. Other variations of the method 200 are possible as well. For example, one or more blocks described above may not be performed in some embodiments. As just one example, the customer's prescription and insurance information may not be displayed for review at block 220, and/or the pharmacist consultation may not be offered at block 224, in some embodiments. Additionally, in some embodiments, one or more of blocks 220, 224, or 232 may be performed after the customer arrives at the prescription pick-up area. For example, one or more of the options provided to the customer at blocks 220, 224, or 232 may be provided to the customer at the prescription pick-up area, and the customer may review prescription and insurance information, accept or decline a pharmacist consultation, and/or pay for his or her order at least partially while the pharmacy technician obtains the customer's order from the order storage area.

Figure 9:
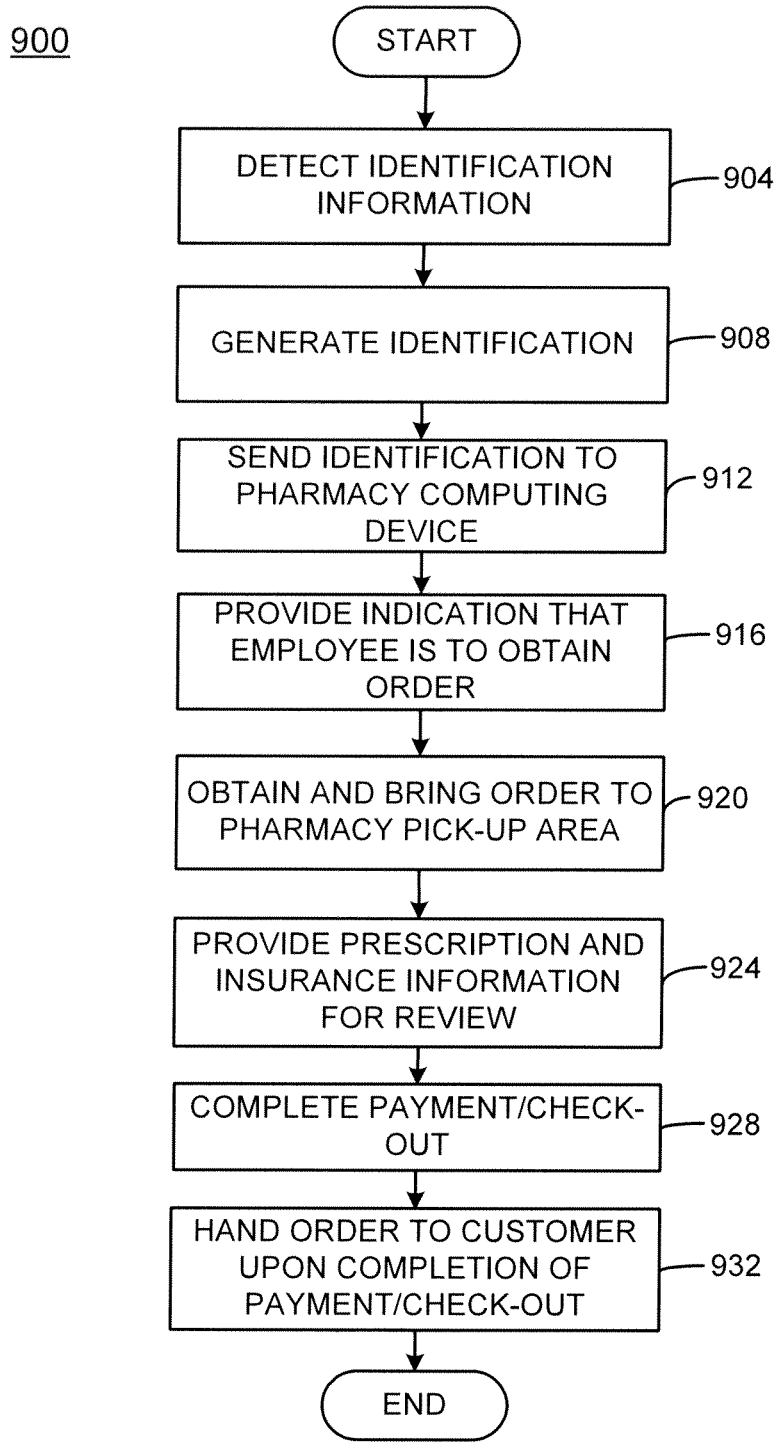
FIG. 9 is a flow chart showing another example method for performing advanced identification of a pharmacy customer, according to an embodiment.

FIG. 9 is a flow chart showing another example method 900 for performing advanced identification of a pharmacy customer. For ease of explanation, the method 900 will be described with reference to the system 100 of FIG. 1. However, it will be understood that the method 900 may be implemented by a system other than the system 100. Similarly, it will be understood that the system 100 may implement methods other than, or in addition to, the method 900.

At blocks 904 and 908, identification information of the customer may be detected and an identification of the customer may be generated based on the detected identification information. The identification information may be detected at block 904 by a customer detection apparatus 42 and without the use of the kiosk 2. The customer detection apparatus 42 may be communicatively coupled to the computing device 35a, as shown in FIG. 1. For example, the customer's identification information may be detected by a facial recognition technique (such as one of the facial recognition techniques described above), where the customer detection apparatus 42 includes one or more imaging devices (not shown) which capture the customer's facial profile information without the need for the customer to use the kiosk 2 or the biometric information capture apparatus 40. Thus, in some embodiments, the imaging device(s) may be positioned to capture facial images of each customer who enters the pharmacy. For example, the imaging device(s) may include a security camera which is pointed toward the entrance to the pharmacy.

According to another embodiment, the imaging device(s) may be positioned in closer proximity to the prescription pick-up window in order to avoid giving a potentially undesirable and/or unnecessary amount of advance notice to the pharmacy technician of the customer's arrival at the pharmacy. For example, the pharmacy may determine that customers typically spend an appreciable amount of time picking out other products (e.g., non-pharmaceutical products such as bath supplies, kitchen supplies, etc.) before proceeding to the prescription pick-up area. The pharmacy may therefore wish to avoid prompting the pharmacy technician to obtain the customer's refill unless the customer is determined to be in relatively close proximity to the prescription pick-up area. In this situation, the pharmacy technician is still likely to be able to hand the customer's refill to him or her upon payment. In particular, in the method 900, the pharmacy technician may have more time to obtain the customer's prescription because, as a result of the customer not using the kiosk 2, the customer may need to spend time reviewing his or her prescription and insurance information after arriving at the prescription pick-up window. Thus, the customer's refill may still be ready for him or her to pick up as soon as payment is completed.

Of course, the customer's identification information may be detected at block 904 in numerous other ways. For example, the customer detection apparatus 42 may include an RFID terminal (not shown) that may be placed near the pharmacy entrance in order to detect an RFID tag in, for example, the customer's discount or rewards card as soon as he or she enters the pharmacy. In another example, the RFID terminal may detect an RFID tag in the customer's mobile telephone or other wireless device, personal digital assistant, etc. as soon as the customer enters the pharmacy.

In another example embodiment, the pharmacy may have previously obtained the customer's permission to detect unique information broadcast by his or her mobile telephone or other wireless device, personal digital assistant, etc. when the customer arrives at the pharmacy. For example, the pharmacy may have obtained the customer's permission to detect unique information broadcast by a cellular radio transceiver, Wi-Fi transceiver, or Bluetooth transceiver within the customer's mobile telephone. The pharmacy may then use the detected information to generate the identification of the customer at block 908 by comparing the detected information with stored mobile telephone information that the pharmacy may already have on file for various customers.

In yet another example, the customer detection apparatus 42 may include a near field communication (NFC) initiator device that generates the identification of the customer at block 908 based on data contained within a passive NFC target device. In some embodiments, the NFC target device may be included in the customer's mobile telephone, such as in the customer's "smart" phone. In other embodiments, the NFC target device may be provided as a tag or sticker within a card issued to the customer by the pharmacy, such as a discount card or rewards card. In various other embodiments, the NFC target device may be or may be included in a standalone "smart" card issued by the pharmacy to the customer, a key fob issued by the pharmacy to the customer, or the NFC target device may be provided to the customer in any other suitable manner.

The NFC initiator device may generate a radio frequency (RF) signal, and may transmit the RF signal to the NFC target device when the customer positions the NFC target device near the customer detection apparatus 42. For example, the customer detection apparatus 42 may be stationed within the pharmacy and may include an indication to the customer to place the NFC target device or an object containing the NFC target device in sufficient proximity to the customer detection apparatus 42. When the signal from the NFC initiator device reaches the NFC target device, the NFC target device may transmit a responsive signal that uniquely identifies the customer to the NFC initiator device. After appropriately processing the responsive signal received at the NFC initiator device in order to detect identification information of the customer at block 904, the customer detection apparatus 42 and/or the kiosk 2 may generate the identification of the customer at block 908. For example, the customer detection apparatus 42 may compare identification information obtained from processing the responsive signal to stored identification information for various customers of the pharmacy, which stored identification information may be accessed via, for example, the network 22.

Of course, the customer detection apparatus 42 may be configured to detect identification information of the customer using near field communication in any of a number of other suitable manners. As just one additional example, the customer detection apparatus 42 may include an NFC target device and the customer may have an NFC initiator device. In this embodiment, the customer may cause the NFC initiator device to send a suitable signal identifying the customer to the NFC target device of the customer detection apparatus. As an example, the customer may select an appropriate icon on a touch screen display of his or her smart phone to cause an NFC initiator device within the smart phone to generate and send the signal identifying the customer to the NFC target device of the customer detection apparatus 42.

In still other example embodiments, the NFC target device may be passive and may be powered by the signal received from the NFC initiator device. For example, the NFC target device may modulate the signal received from the NFC initiator device with the unique identifying information of the customer and then transmit the modulated signal back to the NFC initiator device, in some embodiments. Additionally, in some embodiments, the customer may be provided with an option to use near field communication to pay for the previously prepared pharmacy order, such as at block 928 described below. With reference to the example method 200, the customer may be provided with a similar option to pay for the previously prepared pharmacy order using near field communication at, for example, block 232.

In any event, at block 912, the identification of the customer may be sent to a pharmacy computing device, such as the computing device 35a. In particular, the customer detection apparatus 42 and/or the kiosk 2 may generate the identification of the customer at block 908 as discussed above and may send this identification to the computing device 35a in a similar manner that the kiosk 2 may transmit a customer identification at block 212.

At block 916, the computing device 35a may then provide an indication to the pharmacy technician that the identified customer has come to the pharmacy to pick up his or her order and that the pharmacy technician is to obtain the customer's order. The indication at block 916 may provided in a similar manner as described with respect to block 216. For example, audible and/or visual alerts may be generated and outputted to the pharmacy technician using, for example, the speaker 37 and/or the display device 36.

From block 916, the flow may proceed to block 920, where the pharmacy technician may use the indication provided at block 916 to obtain and bring the customer's order to the pharmacy pick-up area. In some embodiments, the customer may proceed to the pharmacy pick-up area (e.g., a prescription pick-up window) to complete his or her transaction at least partially while the pharmacy technician obtains and brings the customer's order to the pharmacy pick-up area at block 920.

At block 924, the customer's prescription information and insurance information may be provided to the customer at the pharmacy pick-up area for his or her review. Of course, because by this time the customer is already at the pharmacy pick-up area in some embodiments, the prescription and insurance information may not be provided by the kiosk 2. Instead, for example, a pharmacy employee working at the pharmacy pick-up area may verbally review the prescription and insurance information with the customer. In another embodiment, the customer's prescription information and/or insurance information may be provided to the customer for review via another computing device located at the pharmacy pick-up area. According to another embodiment, the customer's order may have already been delivered to the pharmacy pick-up area by the time the customer arrives at the pharmacy pick-up area. Thus, the customer may review the written prescription and insurance information that are physically included with his or her order. In some embodiments, the customer may also have the option of consulting with an on-duty pharmacist or other employee regarding any questions the customer has, including any questions about his or her prescription or insurance information.

At block 928, the pharmacy technician may complete the check-out process with the customer at the prescription pick-up window. At block 932, the customer's order may be handed to him or her as soon as the check-out process is completed. After block 932, the method 900 may end, and the method 900 may be repeated as needed or desired.

While various examples of the method 900 for advanced identification of a pharmacy customer have been shown and described above, many variations of the example method will be recognized by one of ordinary skill in the art in light of the teaching and disclosure herein. As with the method 200, the various blocks of the method 900 need not be performed at distinct times and in some cases may even be performed simultaneously. As just one example, at least a portion of block 920 may be performed while at least a portion of block 928 is performed. In this example, the customer may complete an automated payment process at the pharmacy pick-up area while the pharmacy technician obtains the order, or, for example, another pharmacy employee may complete the payment process with the customer while the pharmacy technician obtains the order. Other variations of the method 900 are possible as well. For example, one or more blocks described above may not be performed, in some embodiments.

It will be appreciated that various embodiments of the system and methods described herein allow, among other advantages, an advance identification of a customer to be sent to a pharmacy technician when the customer arrives at a pharmacy to pick up an order (e.g., a prescription refill). Thus, the pharmacy technician may obtain the customer's previously prepared pharmacy order and bring the previously prepared pharmacy order to a pharmacy pick-up area before or during the customer's check-out/payment process for the refill, and/or before or during one or more other aspects of a transaction for the previously prepared pharmacy order. As a result, the previously prepared pharmacy order may be handed to the customer as soon as the check-out/payment process is complete, avoiding unnecessary delays or wait times which would occur if the pharmacy technician only began to obtain the customer's previously prepared pharmacy order after the customer had already approached the pharmacy pick-up area and identified himself or herself.

Although the foregoing text sets forth a detailed description of numerous different embodiments, it should be understood that the detailed description is to be construed as exemplary only and does not describe every possible embodiment because describing every possible embodiment would be impractical, if not impossible. In light of the foregoing text, one of ordinary skill in the art will recognize that numerous alternative embodiments could be implemented, using either current technology or technology developed after the filing date of this patent application.

What is claimed is:

1. A system for advanced identification of a customer of a pharmacy, the system comprising:
   (A) a data storage device storing identification information corresponding to a customer of a pharmacy located at a store who has remotely placed a pharmacy order for a prescribed medicine or device but who has not yet picked up the prescribed medicine or device, wherein the store includes a pharmacy pick-up area;
   (B) an initiator device located at the store, wherein the initiator device is configured to transmit a first wireless signal conforming to a first protocol to cause a mobile telephone to respond by wirelessly broadcasting identification information uniquely associated with the customer;
   (C) at least one customer identification device located at the store that is communicatively coupled to the data storage device, the at least one customer identification device configured to:
      (i) wirelessly detect a second signal carrying identification information that was wirelessly broadcasted by the mobile telephone associated with the customer after an arrival of the customer at the store and before an arrival of the customer at the pharmacy pick-up area to pick up the pharmacy order, the mobile telephone located at a second area substantially near an entrance of the store, wherein the detected signal conforms to a second protocol different from the first protocol, and wherein the second protocol is selected from the group consisting of: a wi-fi protocol, a Bluetooth protocol, a cellular protocol, and an NFC protocol;
      (ii) generate an identification of the customer by comparing the wirelessly detected identification information to the stored identification information; and
      (iii) transmit the identification of the customer;
   (D) an output device configured to provide at least one of: visual output or audio output, the output device located at the store; and
   (E) one or more computing devices located at the store, the one or more computing devices communicatively coupled to the at least one customer identification device and to the output device, the one or more computing devices configured to:
      (i) receive the identification of the customer from the at least one customer identification device; and
      (ii) cause the output device to generate an audible or visual indication to an employee of the pharmacy, after receiving the identification of the customer from the at least one customer identification device and before the arrival of the customer at the pharmacy pick-up area, that the employee of the pharmacy is to obtain the prescribed medicine or device pharmacy order for pick-up by the customer.

2. The system of claim 1, wherein the at least one customer identification device comprises a self-service kiosk, wherein the self-service kiosk is further configured to provide at least one of: (i) information regarding the pharmacy order for review by the customer before the arrival of the customer at the pharmacy pick-up area, (ii) an option for the customer to schedule a consultation with a pharmacist regarding the pharmacy order before the arrival of the customer at the pick-up area of the pharmacy, or (iii) one or more options for the customer to pay for the pharmacy order using the self-service kiosk.

3. The system of claim 1, wherein the at least one customer identification device comprises a device configured to capture biometric information of the customer, wherein the at least one customer identification device is further configured to compare the captured biometric information of the customer to stored biometric information of the customer and stored biometric information of at least one other customer of the pharmacy in order to generate the identification of the customer.

4. The system of claim 1, wherein the computing device is located in an area of the store where the pharmacy order of the customer is kept before the arrival of the customer at the store.

5. The system of claim 1, wherein the one or more computing devices include a first computing device located at the store, wherein the at least one customer identification device comprises:
   a kiosk located at the store, wherein the kiosk is configured to wirelessly detect the signal carrying the identification information associated with the customer; and
   a second computing device located off-site from the store and communicatively coupled to the kiosk, wherein the second computing device is configured to:
      (i) use the identification information of the customer to generate the identification of the customer; and
      (ii) send the identification of the customer to the first computing device via a communication network.

6. The system of claim 1, wherein the output device is mounted to a wall in order to increase a visibility of the output device to the employee of the pharmacy from within an area of the store where the pharmacy order of the customer is kept before the arrival of the customer at the store.

7. A system including:
(A) a computing device including an output device and located at a pharmacy pick-up area within a store; and
(B) an initiator device located at the store, wherein the initiator device is configured to transmit a first wireless signal conforming to a first protocol to cause a mobile telephone to respond by wirelessly broadcasting identification information uniquely associated with the customer;
(C) a customer identification device that is communicatively connected to the computing device and that:
  (i) wirelessly detects a second signal carrying the identification information, wherein the identification information corresponds to stored identification information for a customer who has remotely placed a pharmacy order for a prescribed medicine or device but who has not yet picked up the prescribed medicine or device, and wherein the second signal was wirelessly broadcasted by the mobile telephone while the mobile telephone was located at a second area substantially near an entrance of the store, wherein the detected second signal conforms to a second protocol different from the first protocol, and wherein the second protocol is selected from the group consisting of: a wi-fi protocol, a Bluetooth protocol, a cellular protocol, and an NFC protocol; and
  (ii) transmits, in response to detecting the identification information, an identification of the customer to the computing device at the pharmacy pick-up area to cause the computing device to provide, via the output device, an audible or visual indication to obtain the prescribed medicine or device for pick-up by the customer.

* * * * *